United States Patent [19] [11] Patent Number: 4,619,133
Kautz et al. [45] Date of Patent: Oct. 28, 1986

[54] SYSTEM FOR CHECKING INSPECTION MACHINES

[75] Inventors: Ralf-Dieter Kautz, Bochum; Rolf Stapelmann, Castrop-Rauxel, both of Fed. Rep. of Germany

[73] Assignee: Holstein und Kappert GmbH, Wambel, Fed. Rep. of Germany

[21] Appl. No.: 644,330

[22] Filed: Aug. 24, 1984

[30] Foreign Application Priority Data

Aug. 26, 1983 [DE] Fed. Rep. of Germany ....... 3330817

[51] Int. Cl.$^4$ .............................................. G01C 25/00
[52] U.S. Cl. ...................................................... 73/1 R
[58] Field of Search ............. 73/1 R, 432 G; 209/523, 209/524, 525, 526, 527, 528, 529, 530; 356/243, 240, 427, 428; 250/252.1; 141/83, 94, 95, 196

[56] References Cited

U.S. PATENT DOCUMENTS

| 2,791,696 | 5/1957 | Schell | 356/427 X |
| 3,589,513 | 6/1971 | Atkinson | 209/525 |
| 3,999,866 | 12/1976 | Mathisen | 356/243 |
| 4,259,020 | 3/1981 | Hanscom | 356/243 |

Primary Examiner—Jerry W. Myracle
Attorney, Agent, or Firm—Toren, McGeady, Stanger, Goldberg & Kiel

[57] ABSTRACT

For the automatic checking of the operational accuracy of inspection machines used in a bottle inspection operation, a star wheel with angularly spaced pockets for the bottles is rotated past testing heads. One or more checking parts are positioned relative to the star wheel to provide an automatic check of the accuracy of the inspection afforded by the testing heads. The checking operation can be effected without interrupting the inspection procedure. The checking can be performed continuously or at specific intervals. Accordingly, a continuous check can be kept on the inspection procedure, in particular without the use of test bottles.

8 Claims, 5 Drawing Figures

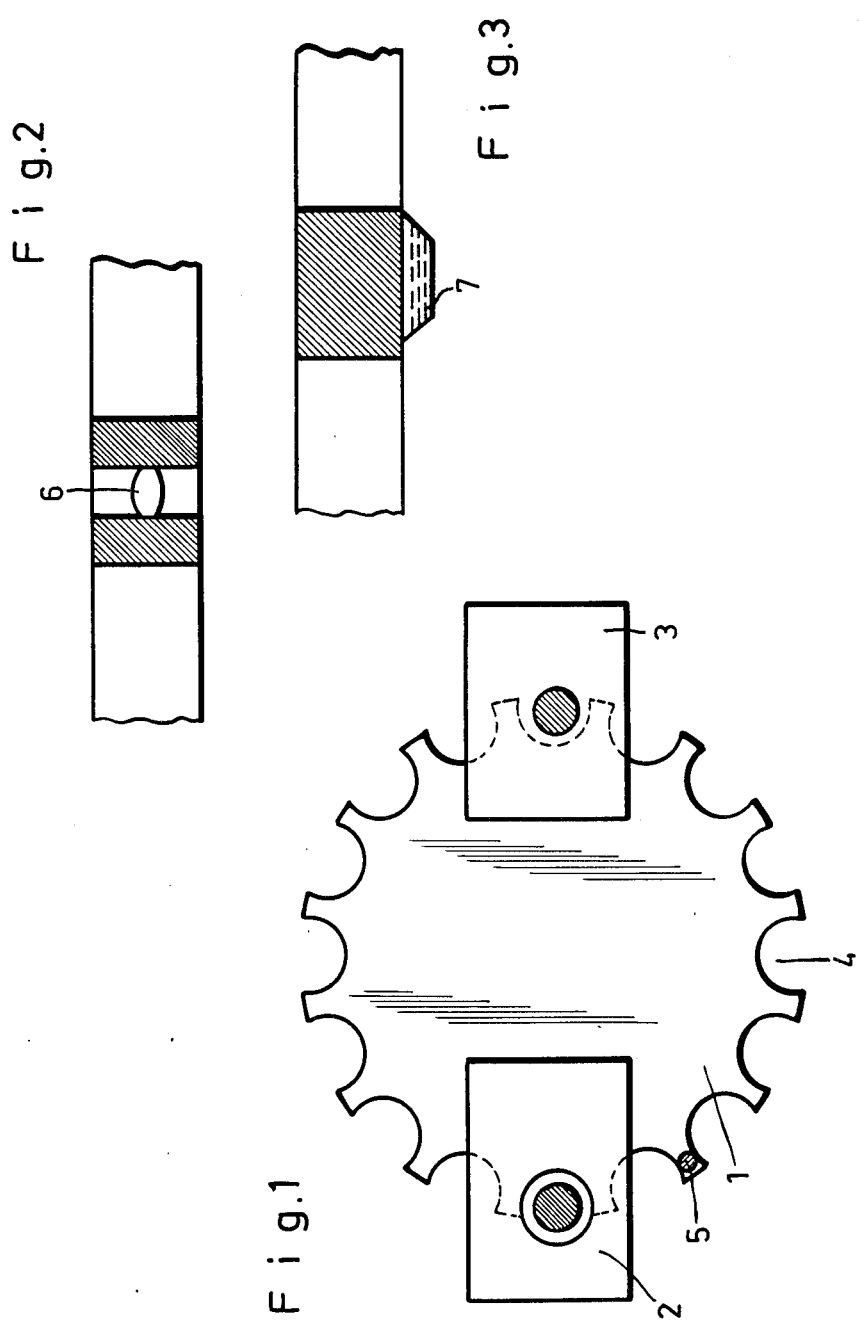

SYSTEM FOR CHECKING INSPECTION MACHINES

SUMMARY OF THE INVENTION

The present invention is directed to a system for checking the operational accuracy of inspection machines, such as bottle inspection machines where bottles supported in the holding pockets of a rotating star wheel are moved past one or more inspecting heads.

Preferably, inspection machines are constructed as rotating members and are equipped with a testing device through which the bottles pass. In such a testing device, several test functions can be carried out and preferably such functions relate to testing the bottom, the opening and the side walls of the bottles which are checked for impurities or foreign particles, such as remaining washing liquid. After a period of time the testing or inspecting function may provide different reaction characteristics and, accordingly, it is necessary to check the test readings at specific time intervals and, if necessary, make an appropriate readjustment of the individual testing devices. Such a procedure entails considerable work. While such procedure is being performed, the normal production must be interrupted. Usually individual test bottles are inserted manually into the usual testing path and must be moved through the testing device where the checking procedure is repeated depending on the number of inspection operations performed by the individual inspection or testing heads. Checking for the inspection accuracy is also dependent on the reliability of the operating personnel, with the result that it may happen that the checking intervals are carried out less frequently than specified under the inspection requirements.

Therefore, it is the primary object of the present invention to check automatically the operational accuracy of the inspection procedure and to carry out the checking operation at specific intervals without requiring that the checking be dependent on the operating personnel. Particularly, a feature of the present invention is to avoid the use of test bottles.

In accordance with the present invention, the star wheel, which normally carries the bottles to be tested, is moved in the normal manner and testing or checking parts are moved along with it so that an automatic checking of the inspection operations can be carried out at specific intervals or continuously.

In one arrangement, it has proven to be advantageous to locate the checking parts between and in the region of the bottle holding pockets in the star wheel.

In another arrangement, the checking parts can be positioned on a separate supporting device, located outside the range of travel of the star wheel, with the checking parts supported so that they can be pivoted into the range of the inspection operation.

In accordance with the present invention, it is possible to carry out the fully automatic check of the operational accuracy of the inspection machine without the use of test bottles. As an additional and special feature, the checking operation can be performed during the normal inspection procedure and the effectiveness of the operating personnel is not important. To assure that the functioning of the checking devices is as free of interference as is possible, the sensitivity of the various checking or testing parts can be adjusted to the appropriate requirements.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWING

In the drawing:

FIG. 1 is a schematic top view of a rotatable star wheel with associated inspection heads;

FIG. 2 is a side view of a portion of a checking part;

FIG. 3 is a schematic view of another checking part for detecting the presence of washing liquid;

DETAILED DESCRIPTION OF THE INVENTION

In FIG. 1 a bottle inspection machine is shown schematically and includes a rotatable star wheel 1 with inspection heads 2 and 3 arranged in the path of the star wheel. The inspection heads may be associated with other inspection devices. Inspection heads 2, 3 test the bottom and the opening of the bottles and are suitable when intergrated with other units, for testing or inspecting the walls and any washing liquid remaining in the bottles, not shown. About its circumferential periphery, the star wheel 1 has uniformly angularly spaced holding pockets in which the bottles to be inspected are positioned. This arrangement of the pockets 4 in the star wheel 1 permits for the proper guidance of the bottles through the inspection operation.

Figure 4:
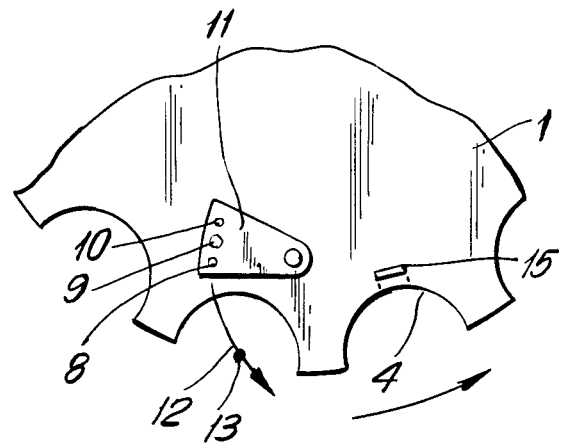
FIG. 4 is a partial schematic top view of the rotatable star wheel shown in FIG. 1 with a pivotally displaceable plate for checking parts.

As shown in FIGS. 1, 2 and 3, checking parts 5, 6 and 7 can be moved along with the star wheel 1. As shown in the drawing, the checking parts 5, 6 and 7 are located between the holding pockets 4 at the circumferential periphery of the star wheel outside of the pockets where the bottles to be inspected are carried. Though not shown, it is also possible to position the checking parts outside of the path of the star wheel on another supporting device, not shown, which moves at the normal rotational speed of the inspection device or of the star wheel 1 and does not interfere with the normal operation of the inspection device. If an additional supporting device is employed, checking parts 8, 9, 10 may be supported as as shown in FIG. 4 so that they can be pivoted on a support plate 11 into the checking position whereby a special checking operation can be effected at the location where the bottles would be otherwise moving along the normal inspection path. The checking parts 5, 6 and 7 are variable in their sensitivity and volume and can be set up and adjusted to the various sensitivities of the testing heads in the inspection device. Checking parts 8, 9, 10 are also of different sizes fixed on the support plate 11 which may be formed of plexiglass. In FIG. 3 the checking part 7 is used for detecting any remaining washing liquid. The checking part 7 copies the actual lower bottle bottom in which the liquid to be inspected and/or the liquid level can be adjusted to a desired height.

Figure 5:
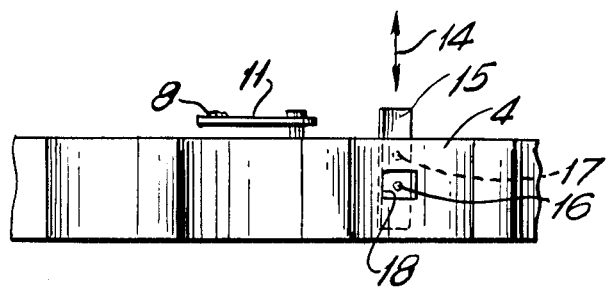
FIG. 5 is a partial side view of the star wheel with a vertically displaceable support member for checking parts.

With the direct coordination of the individual checking parts 5, 6 and 7 with the rotatable star wheel 1, during otherwise normal operation, a check of the operational accuracy of the inspection device can be carried out automatically at specified time intervals or continuously without interrupting the normal inspection operation. On the other hand, in particular if an additional supporting device is utilized, such as in FIG. 4, it is possible to mount the checking parts so that they can be pivoted whereby the checking parts can be set exactly to correspond to the positions of the bottles during normal operation. In such an arrangement, the normal inspection of the bottles is interrupted for a short period of time and is restarted after checking for the accuracy of the inspection machines. If the additional supporting device is not pivotally arranged, the checking for operational accuracy of the inspection device or devices can be performed during normal operations, that is, when the star wheel 1 is filled with bottles. Different modifications of this system can be effected within the scope of the invention, particularly it is conceivable to arrange the entrained checking parts in various regions within the star wheel without departing from the basic concept of the invention. As an example, in FIG. 5 checking parts 16, 17 can be located on a vertically movable support strip 15, for movement in the direction of the arrow 14, into or out of the one of the pockets 4. In the support strip 15 the checking parts 16, 17 can be selectively positioned in the window 18 for affording the desired testing.

While specific embodiments of the invention have been shown and described in detail to illustrate the application of the inventive principles, it will be understood that the invention may be embodied otherwise without departing from such principles.

We claim:

1. A system for checking the operational accuracy of an inspection machine, such as a bottle inspection machine, comprising at least one inspection head, and a rotatable star wheel having spaced bottle holding pockets for conducting bottles past said at least one inspection head, wherein the improvement comprises at least one checking part is arranged relative to said star wheel for movement with said star wheel during normal operation for effecting an automatic checking of the operational accuracy of said at least one inspection head, said holding pockets in said star wheel are located in angularly spaced relation around the circumferential periphery of said star wheel, and said at least one checking part is located in said star wheel at the circumferential periphery thereof and between adjacent said bottle pockets.

2. A system, as set forth in claim 1, wherein said at least one checking part is arranged for effecting the checking operation at specific time intervals.

3. A system, as set forth in clailm 1, wherein said at least one checking part is arranged for effecting the checking operation continuously.

4. A system, as set forth in claim 1, wherein a supporting device is provided separate from said star wheel, a plurality of said checking parts are located on said supporting device outside the range of the inspection operation on said star wheel.

5. A system for checking the operational accuracy of an inspection machine, such as a bottle inspection machine, comprising at least one inspection head, and a rotatable star wheel having spaced bottle holding pockets for conducting bottles past said at least one inspection head, wherein the improvement comprises at least one checking part is arranged relative to said star wheel for movement with said star wheel during normal operation for effecting an automatic checking of the operational accuracy of said at least one inspection head, and said at least one checking part is pivotally supported on said star wheel for pivotal movement into the range of the inspection operation.

6. A system, as set forth in claim 5, wherein said at least one checking part can be located in the inspection position of said bottles as determined by said bottle pockets in said star wheel.

7. A system for checking the operational accuracy of an inspection machine, comprising at least one inspection head, and a rotatable star wheel having spaced bottle holding pockets for conducting bottles past said at least one inspection head, wherein the improvement comprises at least one checking part is arranged relative to said star wheel for movement with said star wheel during normal operation for effecting an automatic checking of the operational accuracy of said at least one inspection head, and said at least one checking part comprises a number of checking parts each of a different size.

8. A system for checking the operational accuracy of an inspection machine, such as a bottle inspection machine, comprising at least one inspection head, and a rotatable star wheel having spaced bottle holding pockets for conducting bottles past said at least one inspection head, wherein the improvement comprises at least one checking part is arranged relative to said star wheel for movement with said star wheel during normal operation for effecting an automatic checking of the operational accuracy of said at least one inspection head, said inspection machine includes at least one inspection head for checking the presence of residual washing liquid, said at least one checking part is arranged for determining the operational accuracy of said inspection head for residual washing liquid, and said checking part reproduces the lower bottle bottom in which one of the checking liquid and/or level of the checking liquid is maintained adjustable.

* * * * *